United States Patent [19]
Tanaka

[11] Patent Number: 5,347,993
[45] Date of Patent: Sep. 20, 1994

[54] BODY CAVITY DIAGNOSTIC APPARATUS

[75] Inventor: Toshizumi Tanaka, Omiya, Japan

[73] Assignee: Fuji Photo Optical Co., Ltd., Saitama, Japan

[21] Appl. No.: 19,254

[22] Filed: Feb. 18, 1993

[30] Foreign Application Priority Data

Feb. 20, 1992 [JP] Japan .................. 4-070349
Feb. 20, 1992 [JP] Japan .................. 4-070350

[51] Int. Cl.$^5$ .................................. A61B 8/12
[52] U.S. Cl. ...................... 128/4; 128/662.06
[58] Field of Search ........................ 128/4-8, 128/662.06, 908

[56] References Cited

U.S. PATENT DOCUMENTS

| | | | |
|---|---|---|---|
| 4,742,818 | 5/1988 | Hughes et al. | 128/4 X |
| 4,777,524 | 10/1988 | Nakajima et al. | 128/4 X |
| 5,201,908 | 4/1993 | Jones | 128/4 |

Primary Examiner—Francis Jaworski
Attorney, Agent, or Firm—Ronald R. Snider

[57] ABSTRACT

A body cavity diagnostic apparatus which is applied to an ultrasonic probe or an endoscope inserted into a cavity of a patient's body. The main body of the apparatus is electrically isolated from the patient completely. Two insulating covers are placed over a structural member in such a manner as to overlap each other at the connecting portion for a bent portion and an operating portion. An annular airtight member such as an O ring, or an annular protrusion integrally provided with the inner insulating cover is provided between the two insulating covers in order to prevent the ingress of a fluid. An insulating member is provided between an electrically conductive member of the insert portion and a base plate for a support shaft of the operating portion. Operating wires are connected to each other by a joint member of an insulating material, thereby electrically isolating the operating portion from the bent portion.

11 Claims, 7 Drawing Sheets

PRIOR ART

Fig.9

PRIOR ART

Fig.10

BODY CAVITY DIAGNOSTIC APPARATUS

BACKGROUND OF THE INVENTION

This application claims the priority of Japanese Patent Application Nos. 4-70349, and 4-70350 filed on Feb. 20, 1992, which are incorporated herein by reference.

FIELD OF THE INVENTION

The present invention relates to a body cavity diagnostic apparatus applied to an ultrasonic probe, an endoscope or the like which is inserted in a cavity of the body of a patient so as to display an image of the object of inspection on a monitor, more particularly, to the structure of such a body cavity diagnostic apparatus for electrically isolating the apparatus from the patient.

DESCRIPTION OF THE RELATED ART

A body cavity (ultrasonic) diagnostic apparatus has been used to noninvasively diagnose a diseased part by inserting an ultrasonic probe into a body cavity, and emitting ultrasonic beams to the object of inspection therein so as to display a tomographic image of the object on a monitor. As a body cavity diagnostic apparatus, there are, for example, an apparatus for displaying a tomographic image in a comparatively wide region by singly inserting an ultrasonic probe having a predetermined diameter into a cavity of the body such as a digestive organ, and an apparatus for displaying a tomographic image by inserting an ultrasonic probe having a small diameter in the shape of a catheter into a forceps insertion hole which is provided in an electronic endoscope for picking up an image by a CCD, (Charge Coupled Device) as a solid-state image sensor.

Figure 9:
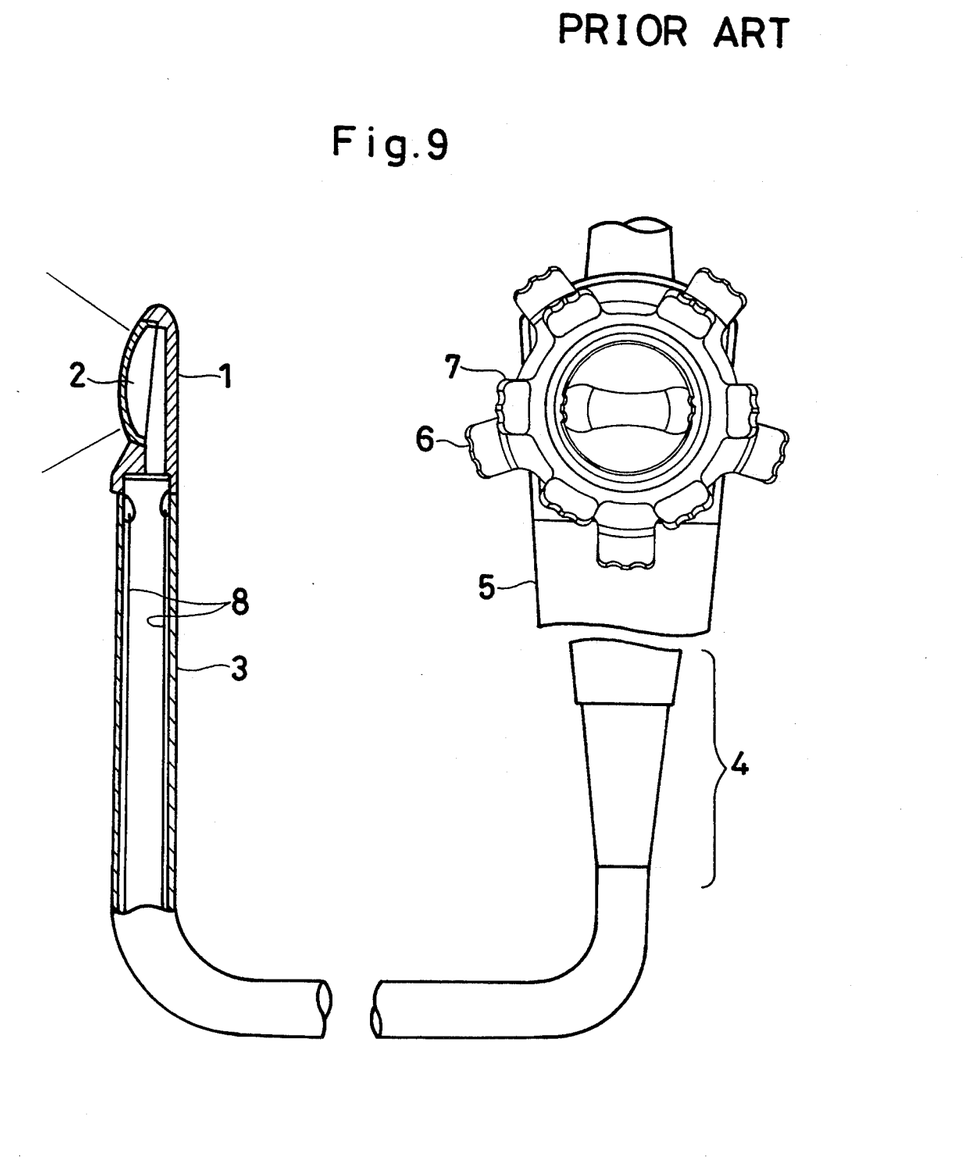
FIG. 9 shows the entire structure of a conventional body cavity diagnostic apparatus.

FIG. 9 schematically shows the structure of a conventional body cavity diagnostic apparatus (transesophagus probe). As shown in FIG. 9, a dumbbell-shaped oscillator 2 is provided on the side surface of a forward end portion 1 so as to emit predetermined ultrasonic beams by controlling the oscillation of a plurality of oscillating elements. The forward end portion 1 is held by a bent portion 3 and connected to an operating portion 5 through a connecting portion 4 at the rear end. By operating the operating portion 5 it is possible to bend the forward end portion 1 both in the vertical and in the horizontal direction. More specifically, the operating portion 5 is provided with a vertically angling knob 6 and a horizontally angling knob 7. These angling knobs 6, 7 are connected to the forward end portion 1 by four wires 8. By pulling the wires 8 by turning the vertically angling knob 6 and the horizontally angling knob 7, it is possible to bend the forward end portion 1 in the required direction. Thus, according to this body cavity diagnostic apparatus, a tomographic image of the diseased part is produced by emitting ultrasonic beams to the predetermined region while positioning the forward end portion 1 at the object of inspection by the operation of the operating portion 5.

In such a diagnostic apparatus, since the forward end portion 1 and the bent portion 3 are inserted in a cavity of the patient's body, it is necessary to hold the inserted portion in the electrically insulated (floating) state for the safety of the patient. In a conventional diagnostic apparatus, therefore, the forward end portion 1 and the bent portion 3 are covered with a resin (plastic) material or an elastic rubber material, which is an insulator.

Figure 10:
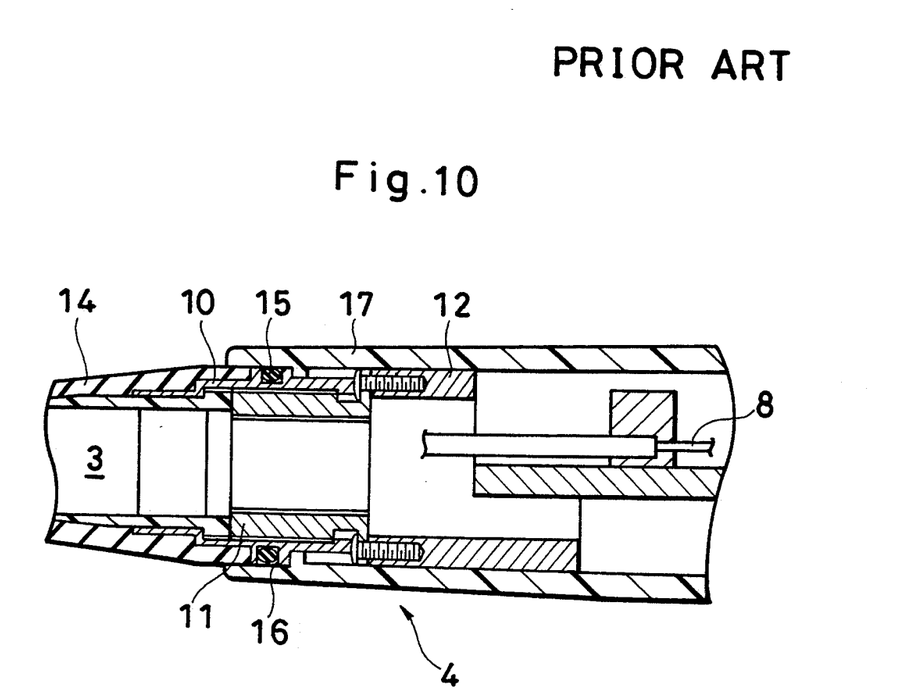
FIG. 10 is a sectional view of the structure of the connecting portion for connecting the bent portion and the operating portion shown in FIG. 9.

In a conventional body cavity diagnostic apparatus, however, although measures for electrically insulating the forward end portion 1 and the bent portion 3 which are inserted into a cavity of the body are taken in their own ways, the insulating measures for the connecting portion at the rear end of the bent portion 3 and the subsequent processing units is not sufficient. FIG. 10 shows the internal structure of the connecting portion 4 at the rear end of the bent portion 3 shown in FIG. 9. As shown in FIG. 10, a first (outer) metal fixing cylinder 10 for holding the bent portion 3 with the rear end portion passed therethrough is provided. A second (inner) metal fixing cylinder 11 which is screwed into the first fixing cylinder 10 is fixed to a metal cylinder 12 of the operating portion 5 side by screws or the like. The bent portion 3 is connected to the operating portion 5 by fixing the second fixing cylinder 11 to the cylinder 12 by screws after passing the rear end portion of the bent portion 3 through the first fixing cylinder 10 so that the rear end portion is held by the first fixing cylinder 10.

The first fixing cylinder 10 is integrally provided with a rubber boot 14 which is a part of the insulating cover, and a groove 16 for holding an O ring 15 is provided at a predetermined position of the outer periphery of the first fixing cylinder 10. The assembly of the connecting portion 4 at the rear end of the bent portion 3 is completed by fitting the O ring 15 into the groove 16 and placing a resin (plastic) cover 17 over the rubber boot 14 in close contact therewith.

In the above-described assembly, however, since the airtightness between the rubber boot 14 on the bent portion 3 side and the cover 17 on the operating portion 5 side is not sufficient, a fluid or the like enters through the gap between the rubber boot 14 and the cover 17 and reaches as far as the first metal fixing cylinder 10. As a result, it is impossible to maintain the electrical isolation of the patient from the internal electric circuit. Such ingress of a fluid occurs not only at the rear end of the bent portion 3 but also at various joints in various diagnostic apparatuses. In recent years, a body cavity diagnostic apparatus has often been used during a surgical operation. In such a case, physiological saline solution, body fluids, blood or the like is expected to enter and reach the connecting portion 4 at the rear end of the bent portion 3 or other various connecting portions. It is thus necessary to consider a countermeasure.

SUMMARY OF THE INVENTION

Accordingly, it is an object of the present invention to eliminate the above-described problems in the related art and to provide a body cavity diagnostic apparatus which is capable of electrically floating the insert portion from a patient sufficiently by enhancing the airtightness between two insulating covers provided on the outside of a metal member and electrically isolating the operating portion and its base plate from the electrically conductive members on the inside of the insert portion.

To achieve this aim, a body cavity diagnostic apparatus according to the present invention comprises: two insulating covers which are connected in such a manner as to overlap each other on the outside of the metal members which constitute the structural part of the main body of the apparatus; and an annular airtight member which is disposed between the insulating covers. In the inner one of the two insulating covers, a groove for holding the airtight member therein, for example, an O ring, is formed, and the two insulating covers with the O ring fitted into the groove are placed over the metal members. According to this structure, since the O ring is received and held by the inner insulating cover, and the outer insulating cover is placed thereover in close contact with the O ring, the airtightness is maintained not between the metal member and the outer cover as in the conventional apparatus but between the inner and the outer insulating covers, thereby preventing a fluid or the like from entering and reaching the metal members from the outside.

It is also possible to integrally form an annular protrusion which serves as the O ring on the inner cover and place the outer insulating cover thereover in close contact with the annular protrusion. According to this structure, the O ring is formed on the inner insulating cover itself, and the airtightness is therefore maintained between the inner and the outer insulating covers in the same way as in the above.

Furthermore, the body cavity diagnostic apparatus according to the present invention is provided with wires connecting the end of the insert portion which is inserted to a body cavity of a patient to the operating portion so as to bend the forward end portion in a predetermined direction by the wire-pulling operation of the operating portion, and an electrically conductive base plate for a support shaft in the operating portion is connected to an electrically conductive structural member with an insulating member therebetween. According to this structure, the internal structural member on the insert portion side is electrically insulated from the base plate of the operating portion.

In addition, the wires which connect the operating portion and the forward end portion are connected to each other by a joint member of an insulating material so as to electrically insulate the operating portion from the forward end portion. According to this structure, the wires are electrically isolated from each other by the joint member of an insulating material, for example, between the operating portion and the forward end portion, and the operating portion and its base plate are therefore floated from the insert portion which is composed of the forward end portion and a bent portion.

In this case, wire guides for guiding the wires in the insert portion are provided. It is preferable to attach each of the wire guides to the electrically conductive base plate by an attaching member or the like which is made of an insulating material.

These structures are appropriately combined in order to complete the electric insulation.

The above and other objects, features and advantages of the present invention will become clear from the following description of the preferred embodiments thereof, taken in conjunction with the accompanying drawings.

DESCRIPTION OF THE PREFERRED EMBODIMENTS

First Embodiment

Figure 1:
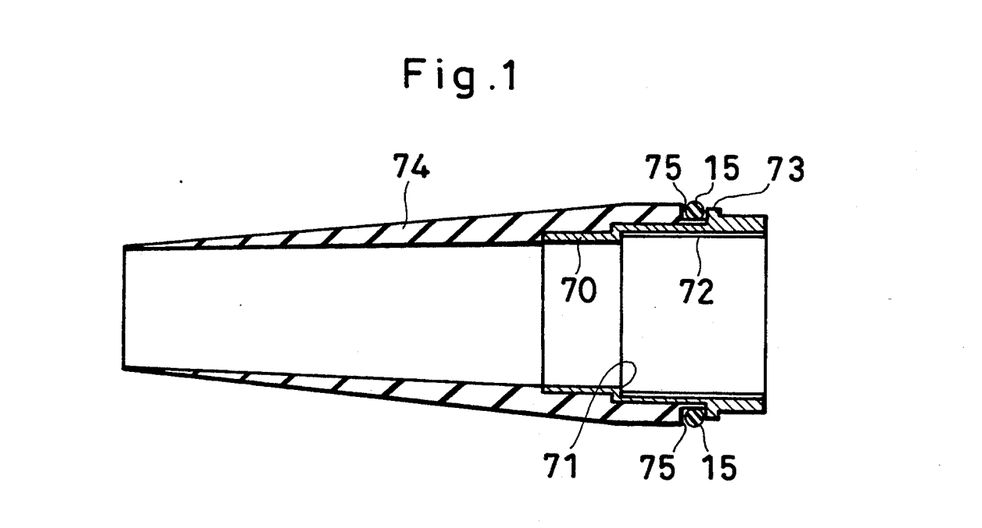
FIG. 1 is a sectional view of a first fixing cylinder and a rubber boot which are used at a connecting portion (for connecting the bent portion and the operating portion) of a first embodiment (transesophagus probe) of a body cavity diagnostic apparatus according to the present invention.
Figure 2:
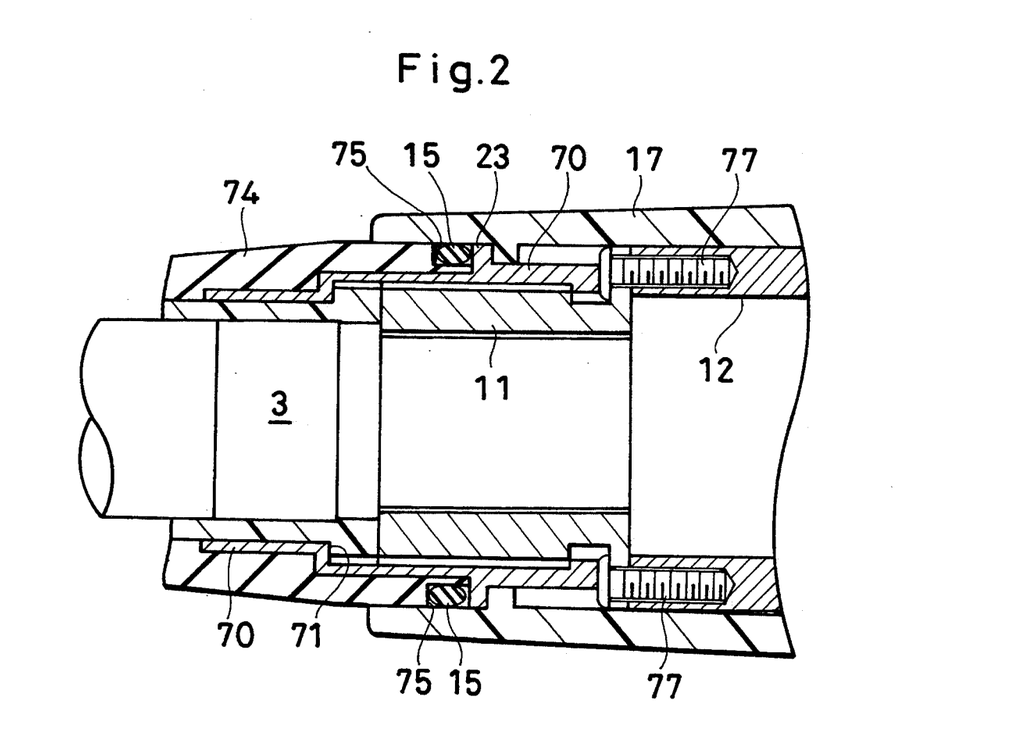
FIG. 2 is an enlarged sectional view of the operating portion of the first embodiment at which the bent portion is connected to the operating portion.

FIGS. 1 and 2 show the structure of a first embodiment (transesophagus probe) of a body cavity diagnostic apparatus according to the present invention. FIG. 1 shows the structure of a first fixing cylinder portion of the bent portion and FIG. 2 shows the first fixing cylinder portion in the assembled state. In FIG. 1, a first fixing cylinder 70 for connecting the bent portion and the operating portion is made of a metal material, and a stepped portion 71 is formed therein so as to retain the bent portion with the rear end portion thereof passed through the first fixing cylinder 70. A female screw portion 72 is formed on the inner surface of the first fixing cylinder 70, and a later-described second fixing cylinder is screwed into the female screw portion 72. An annular protrusion 73 for controlling the position of an O ring 15 is provided on the outer periphery of the first fixing cylinder 70, and a rubber (elastic rubber) boot 74 as an insulating shielding cover is integrally provided at the forward end portion of the first fixing cylinder 70. The rubber boot 74 is further provided with an annular groove 75 for receiving and holding the O ring 15, and, as shown in FIG. 1, the O ring 15 is placed on the position defined by the annular groove 75 and the protrusion 73. Although the annular groove 75 is in the shape of a groove with one side open in this embodiment, the portion which corresponds to the protrusion 73 may also be provided on the rubber boot 74 so as to shape the annular groove 75 like a complete channel.

FIG. 2 shows the assembled first fixing cylinder 70 and rubber boot 74 having the structure shown in FIG. 1. A resin (plastic) cover 17 is provided on the outer periphery of a metal cylinder 12 on the operating portion side, and a second metal fixing cylinder 11 with a male screw portion provided on the outer periphery thereof is fixed to the cylinder 12 by screws 77. The bent portion 3 is first passed through the first fixing cylinder 70 with the O ring 15 set in the annular groove 75 of the rubber boot 74, and the rear end portion of the bent portion 3 is retained at the stepped portion 71. Thereafter the male screw portion of the second fixing cylinder 11 is screwed and fixed into the female screw portion 72 of the first fixing cylinder 70, thereby connecting the bent portion 3 to the operating portion 5 completely. At this time, since the airtightness between the rubber boot 74 and the cover 17 on the operating portion side is effectively maintained by the O ring 15, as shown in FIG. 2, a fluid does not enter as far as the first metal fixing cylinder 70 from the gap between them, thereby ensuring the maintenance of the floating state at the connecting portion of the apparatus.

Second Embodiment

Figure 3:
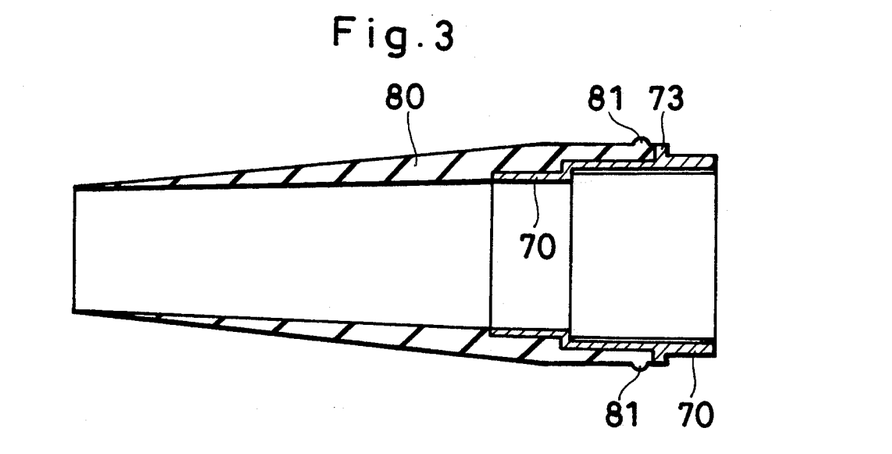
FIG. 3 is a sectional view of a first fixing cylinder and a rubber boot at a connecting portion in a second embodiment according to the present invention.
Figure 4A:
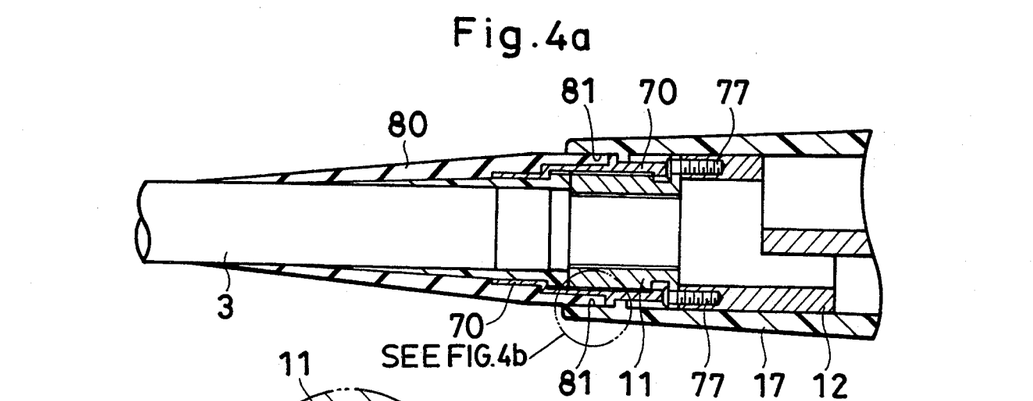
FIG. 4A is a sectional view of the connecting portion of the second embodiment in which the bent portion is connected to the operating portion.
Figure 4B:
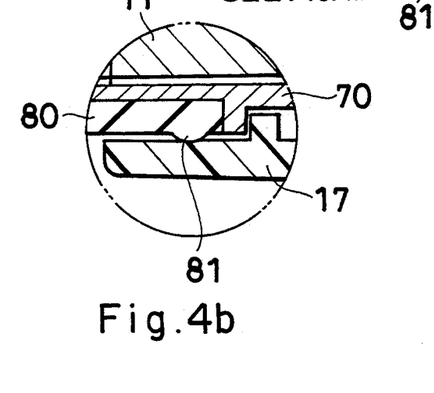
FIG. 4B shows an expanded view of a portion of FIG. 4A.

FIGS. 3 and 4A show the structure of a second embodiment of the present invention. In this embodiment, an O ring is integrally provided with a rubber boot as an insulating shielding cover. As shown in FIG. 3, a rubber boot 80 is integrally provided with the first fixing cylinder 70 which has the same structure as in the first embodiment. In the vicinity of the protrusion 73 of the first fixing cylinder 70, an annular protrusion 81 having a semicircular section which protrudes to a higher degree than the protrusion 73 is integrally provided with the rubber boot 80. The rubber boot 80 is made of an elastic rubber material, and it is preferable to select such an elastic material for the rubber boot 80 as to maintain the airtightness by the annular protrusion 81.

According to the second embodiment, as shown in FIG. 4A, the bent portion 3 is completely connected to the operating portion by passing the bent portion 3 through the first fixing cylinder 70 with the rear end portion thereof rerained at the stepped portion 71 and screwing and fixing the second fixing cylinder 11 into the first fixing cylinder 70 in the same way as in the first embodiment. At this time, since the cover 17 on the operating portion side is in close contact with the annular protrusion 81, the airtightness between the rubber boot 80 and the cover 17 is effectively maintained. Furthermore, in this second embodiment, the labor and time for attaching an O ring is dispensed with.

According to this structure, it is possible to enhance the airtightness between two covers at the connecting portion of the main body of the apparatus, and effectively maintain the electrical insulation in a wide region in the main body of the apparatus. Therefore, it is possible to securely maintain the safety of a patient even if the apparatus is used during a surgical operation.

Although the insulating covers are applied to the connecting portion of the bent portion 3 and the operating portion 5 in the first and second embodiments, they are also applicable to other portions in which two covers are connected to each other in a body cavity diagnostic apparatus.

In addition, although the rubber boots 74, 80 as inner insulating covers are made of an elastic rubber in these embodiments, the inner shielding cover may be made of a resin material. It is also possible to provide the protrusion in a third embodiment on the outer insulating cover 17 side.

Third Embodiment

Figure 5:
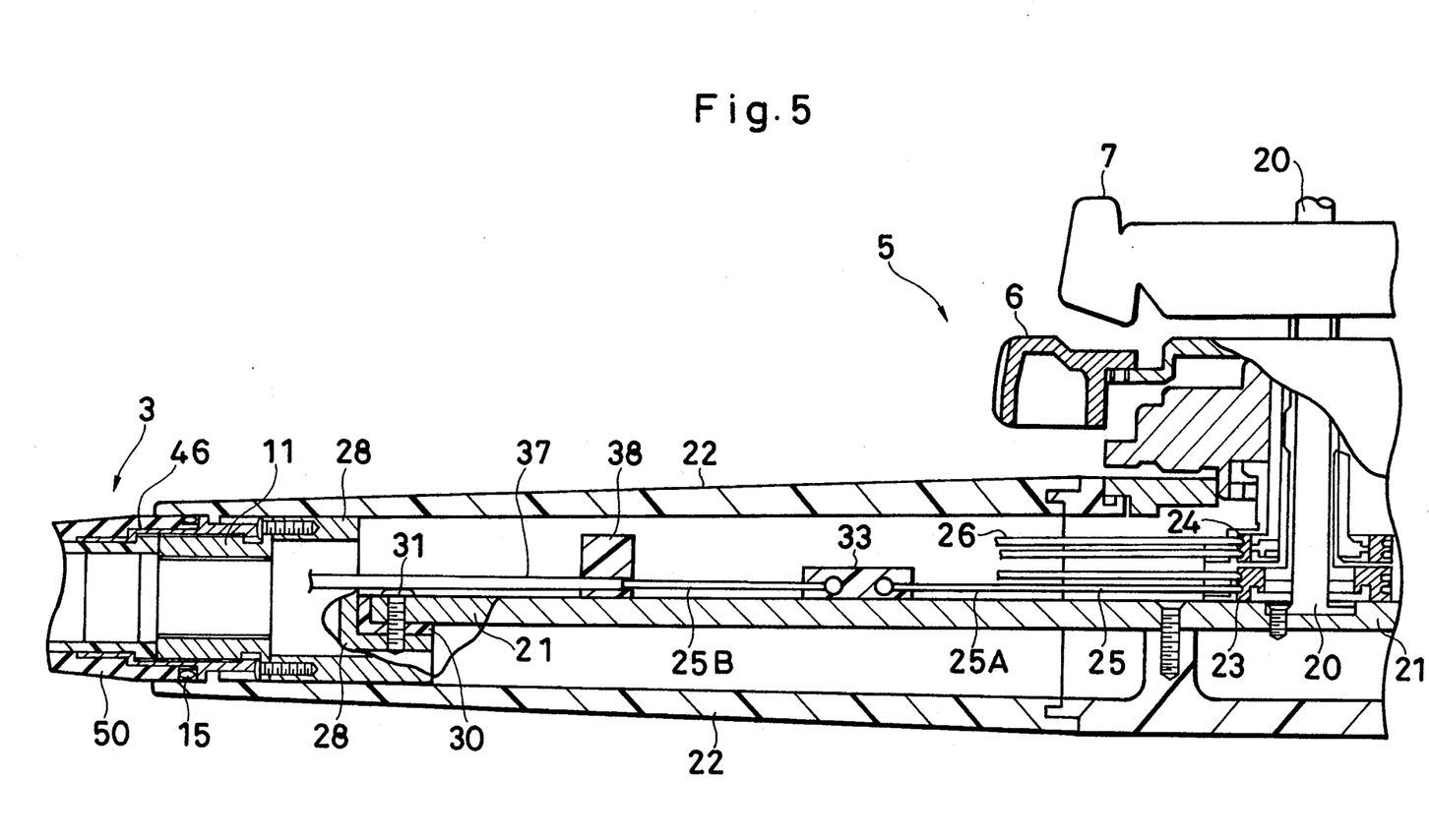
FIG. 5 is a sectional view of the internal structure of a connecting portion of a transesophagus probe, which is a third embodiment of the present invention.

FIG. 5 is a sectional view of the vicinity of the operating portion of a third embodiment (a transesophagus probe) of the present invention. As shown in FIG. 5, the vertically angling knob 6 and the horizontally angling knob 7 which turn round a support shaft 20 are attached to the operating portion 5. The support shaft 20 is fixed on a metal base plate 21 which is connected to an outer case (cover) 22 with screws or the like, and the outer case 22 made of a resin (plastic) material has a size which allows the outer case 22 to be easily held by a hand. Pulleys 23, 24 are connected to the vertically angling knob 6 and the horizontally angling knob 7 through respective cylindrical shaft. Wires 25, 26 which are attached to the pulleys 23, 24 are connected to the forward end portion of the bent portion 3 at four positions through the bent portion 3. The bent portion 3 is provided with an ultrasonic oscillator. Thus, the forward end portion is bent by the operation of pulling the wires 25, 26 by rotating the vertically angling knob 6 and the horizontally angling knob 7.

Figure 6:
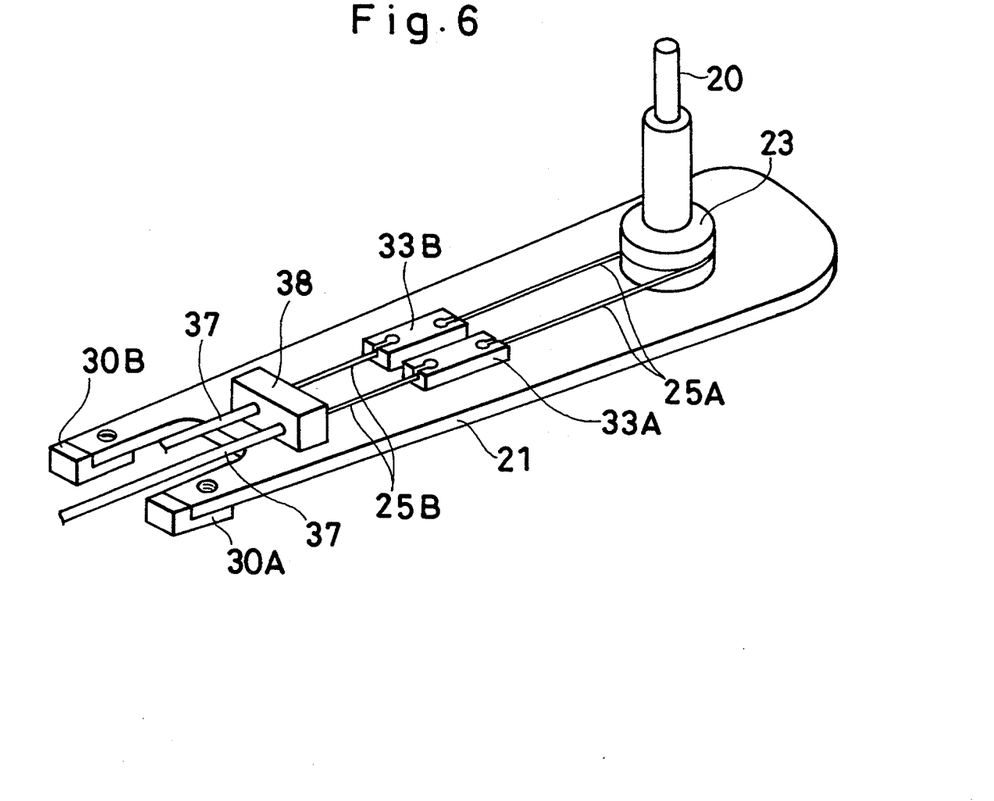
FIG. 6 is a perspective view of the base plate portion of the operating portion in the third embodiment.

The base plate 21 is fixed with screws on both side surfaces of a metal-made supporting cylinder 28 of the bent portion 3 together with resin L-shaped plates 30 which are provided between the base plate 21 and the supporting cylinder 28. FIG. 6 is a perspective view of the base plate 21. As shown in FIG. 6, since the base plate 21 is supported at two portions, namely, on both side surfaces of the supporting cylinder 28, the two L-shaped plates (30A,30B) are provided on the respective side surfaces of the base plate 21, thereby electrically insulating the base plate 21 from the electrically conductive members of the bent portion 3 and the forward end portion which are inserted into a cavity of the body.

Figure 7:
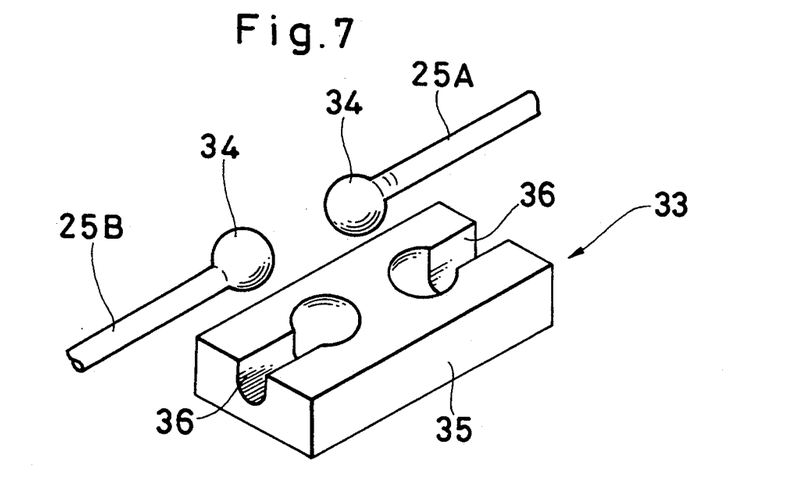
FIG. 7 is an exploded perspective view of the structure of a joint member for wires in the third embodiment.

Measures for electrically insulating the wires 25, 26 from the forward end portion and the bent portion which are inserted into a body cavity are also taken in this embodiment. The measures for insulating the wire 25 will be first explained in the following. As shown in FIG. 5, a wire 25A on the pulley 23 side is connected to a wire 25B on the forward end portion and the bent portion 3 side with a resin (plastic) joint member 33. Spherical head portions 34 are provided at the end portions of the wires 25A, 25B, and two grooves 36 into which the spherical head portions 34 and the subsequent portions of the wires 25A, 25B are fitted are made in such a manner as to face each other in the longitudinal direction of the rectangular parallelepiped main body of the joint member 33, as shown in FIG. 7. Both wires 25A and 25B are connected to each other by fitting the spherical head portions 34 and the wire 25 into the two grooves 36. The connection of the wires 25A and 25B is executed by two joint members 33A and 33B as shown in FIG. 6. The connection of the other wires 26A, 26B is executed by the joint member 33 in the same way.

In addition, measures for electrically insulating wire guides for guiding the wires 25, 26 are taken in the third embodiment. The wire 25 is guided by a metal wire guide 37 in its intermediate portion. The wire guide 37 is provided with a coiled spring (not shown) which is in close contact with the periphery of the wire 25 at the forward end portion. By virtue of the coiled spring, it is possible to adjust the relative position of the wire 25 which is pulled during the operation of bending the bent portion 3 in the vertical direction. The wire guide 37 is fixed to the base plate 21 by a resin (plastic) attaching member 38, thereby maintaining the electrical insulation of the wire guide 37 from the base plate 21.

A wire-guide (not shown) for guiding the other wire 26 is attached on the upper portion of the attaching member 38 in the same way.

Figure 8A:
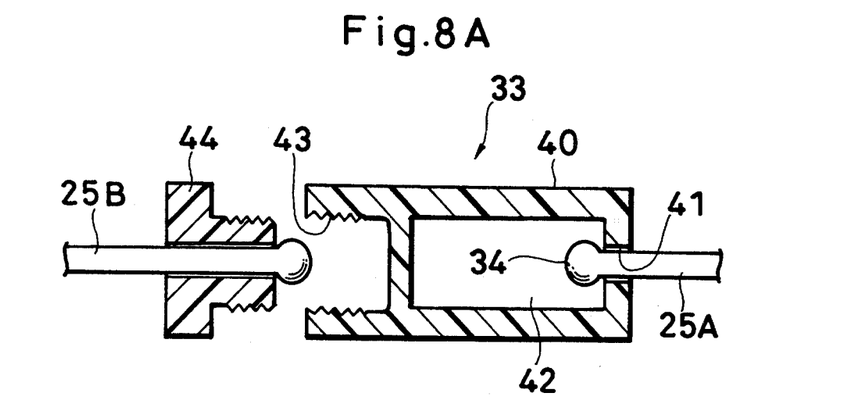
FIG. 8A is a sectional view of another structure of a joint member for wires in the third embodiment.
Figure 8B:
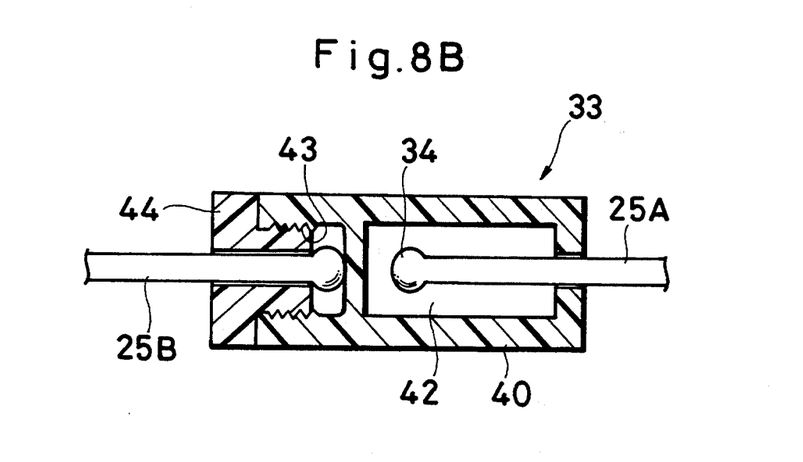
FIG. 8B is a sectional view of the joint member shown in FIG. 8A in the assembled state.

Another example of the joint member 33 for the wires 25 and 26 will be explained in the following with reference to FIGS. 8A and 8B. As shown in FIG. 8A, the rectangular parallelepiped main body 40 of the joint member 33 is provided at one end thereof with a hole 41 for passing the wire 25A (26A) itself therethrough and retaining the spherical head portion 34 therein, and a space 42 for allowing the wire 25A (25B) to move therein in the direction in which the wire 25A (25B) is pulled. At the other end of the joint 40 are provided a female screw portion 43 and a male screw portion 44 having the other wire 25B (25A) passed therethrough and fixed therein. The connection of the wires 25A and 25B is accomplished by screwing the male portion 44 into the female portion 42, as shown in FIG. 8B. According to this embodiment, since the space 42 of the joint member 33 can accommodate some part of the wire 25A (25B), it is possible to prevent the wire 25 from slacking.

As described above, according to the third embodiment, lit is possible to electrically isolate the operating portion and its base plate from the electrically conductive members on the inside of the insert portion side and, hence, electrically insulate a patient from the body cavity diagnostic apparatus sufficiently. It is therefore possible to securely maintain the safety of the patient even if it is used during a surgical operation.

In the third embodiment, although the base plate 21 is electrically insulated from the supporting cylinder 28, if there is any other electrically conductive member which is in contact with the base plate 21 at the forward end portion of the insert portion, an insulating member is disposed between the electrically conductive member and the base plate 21.

The wires 25A, 25B, (26A, 26B) are connected by the joint member 33 in the middle portion of the wire 25 (26) in this embodiment. Alternatively, it is possible to produce a part or the entire part of each of the pulleys 23 and 24 which are disposed on the periphery of the support shaft 20 from an insulating material as a joint member, and to attach the wires 25, 26 to the pulleys 23 and 24, respectively.

Some part of the structures of the first and the second embodiments is also adopted in the third embodiment. In this way it is preferable to combine these structures appropriately.

Although a body cavity diagnostic apparatus according to the present invention is applied to a transesophagus in the above-described embodiments, the present invention is not restricted thereto. For example, the present invention is applicable to an ultrasonic probe which is inserted into the forceps insertion hole of an endoscope or other body cavity diagnostic apparatuses.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A body cavity diagnostic apparatus comprising in combination:
    a main body;
    an inner electrically insulating cover made of an elastic rubber material;
    an outer electrically insulating cover made of synthetic resin;
    members having outsides and which constitute a structural part of said main body;
    wherein said inner and outer insulating covers are connected in such a manner as to overlap each other on said metal member outsides, said apparatus further comprising a bent portion connected to an insert portion, a control portion and a connecting portion for said insert and control portions,
    wherein said inner and outer insulating covers and said annular airtight member are applied to said connecting portion for an operating portion and said bent portion connected to an insert portion which is inserted into a cavity of an object of inspection; and
    an annular airtight member which is disposed between said insulating covers.

2. A body cavity diagnostic apparatus according to claim 1, wherein said annular airtight member is an O ring, and the inner one of said two insulating covers is provided with an annular groove for holding said O ring, said two insulating covers being placed over said metal members with said O ring fitted into said annular groove.

3. A body cavity diagnostic apparatus according to claim 1, wherein the inner one of said two insulating covers is integrally provided with an annular protrusion which serves as an O ring, and the outer insulating cover is placed over said inner insulating cover in close contact with said annular protrusion.

4. A body cavity diagnostic apparatus comprising: an insert portion which is inserted into a body cavity; an operating portion; a wire extending from the forward end of said insert portion to said operating portion so as to be bent in a predetermined direction by a wire-pulling means in said operating portion; and an insulating member for connecting an electrically conductive base plate for a support shaft of said wire-pulling means of said operating portion with an electrically conductive structural member of said insert portion.

5. A body cavity diagnostic apparatus according to claim 4, wherein said insulating member is in the shape of the letter "L".

6. A body cavity diagnostic apparatus comprising: an insert portion which is inserted into a body cavity; and operating portion; wires having heads extending from the forward end portion of said insert portion to said operating portion so as to be bent in a predetermined direction by a wire-pulling operation of said operating portion; and a joint member of an insulating material for connecting at least one of said wires with said operating portion and said forward end portion by said joint member holding the head of one of said wires so as to electrically isolate said operating portion from said forward end portion.

7. A body cavity diagnostic apparatus according to claim 6, wherein said wire includes two wire members, each being provided with a head portion at one end thereof, and said joint member is provided on both sides thereof with a groove into which said head portion and a part of said wire member are fitted.

8. A body cavity diagnostic apparatus according to claim 6, wherein said joint member is provided therein with a space for allowing the connected wire to move in the longitudinal direction so as to accommodate a part of said wire, thereby preventing said wire from slacking.

9. A body cavity diagnostic apparatus according to claim 6, further comprising an insulating member for connecting an electrically conductive base plate for a support shaft of said operating portion with an electrically conductive structural member of said insert portion.

10. A body cavity diagnostic apparatus according to claim 6, further comprising a wire guide for introducing said wire within said insert portion, and an attaching member produced from an insulating material for attaching said wire guide to the electrically conductive base plate of a support shaft of said operating portion.

11. A body cavity diagnostic apparatus comprising in combination:
- a main body;
- an inner electrically insulating cover made of an elastic rubber material;
- an outer electrically insulating cover made of synthetic resin;
- metal members having outsides and which constitute a structural part of said main body;
- wherein said inner and outer insulating covers are connected in such a manner as to overlap each other on said metal member outsides;
- said apparatus further comprising a bent portion connected to an insert portion, a control portion, and a connecting portion for said insert and control portions,
- wherein said inner and outer insulating covers and said annular airtight member are applied to said connecting portion for an operating portion and said bent portion connected to an insert portion which is inserted into a cavity of an object of inspection;
- an annular airtight member which is disposed between said insulating covers;
- an insert portion which is inserted into a body cavity;
- an operating portion;
- a wire extending from a forward end of said insert portion to said operating portion so as to be bent in a predetermined direction by a wire-pulling means in said operating portion;
- an insulating member for connecting an electrically conductive base plate for support shaft of said wire-pulling means of said operating portion with an electrically conductive structural member of said insert portion;
- wires having heads extending from the forward end portion of said insert portion to said operating portion so as to be bent in a predetermined direction by a wire-pulling operation of said operating portion; and
- a joint member of an insulating member for connecting at least one of said wire wires with said operating portion and said forward end portion by said joint member holding the head of one of said wires so as to electrically isolate said operating portion from said forward end portion.

* * * * *